United States Patent [19]

Kühle et al. [45] Feb. 17, 1976

[54] N-SULFENYLATE-N-METHYL-CARBAMIC ACID ESTERS OF 2-OXIMINO-ALKANECARBOXYLIC ACID NITRILES

[75] Inventors: Engelbert Kühle, Berg.Gladbach; Peter Siegle, Cologne; Ingeborg Hammann, Cologne; Wolfgang Behrenz, Cologne, all of Germany

[73] Assignee: Bayer Aktiengesellschaft, Leverkusen, Germany

[22] Filed: Feb. 11, 1974

[21] Appl. No.: 441,599

[30] Foreign Application Priority Data

Feb. 22, 1973    Germany............................ 2308660

[52] U.S. Cl.............................. 260/453 R; 424/298
[51] Int. Cl.²....................................... C07C 119/00
[58] Field of Search......... 260/465 D, 465 D, 465.4, 260/453 R, 453 N

[56] References Cited
UNITED STATES PATENTS

| | | | |
|---|---|---|---|
| 3,483,246 | 12/1969 | Kaufman............................ | 260/465 |
| 3,522,287 | 7/1970 | Donninger et al.............. | 260/465.4 |
| 3,825,579 | 7/1974 | Fujimoto et al................ | 260/453 R |

Primary Examiner—Lewis Gotts
Assistant Examiner—Dolph H. Torrence
Attorney, Agent, or Firm—Burgess, Dinklage & Sprung

[57] ABSTRACT

N-sulfenylated-N-methyl-carbamic acid esters of 2-oximino-alkanecarboxylic acid nitriles of the formula

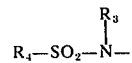

in which
$R_1$ is alkyl, cycloalkyl, or alkyl-substituted cycloalkyl, and
$R_2$ is a $C_{1-8}$ aliphatic radical substituted by halogen; aryl; aryl substituted by halogen, methyl, trifluoromethyl or nitro; or the radical of the formula $$R_4-SO_2-\underset{\underset{\displaystyle R_3}{|}}{N}-$$

wherein
$R_3$ is alkyl, and
$R_4$ is alkyl, haloalkyl, aryl, or aryl substituted by halogen, methyl or nitro,
which possess insecticidal, acaricidal, fungicidal and bactericidal properties.

7 Claims, No Drawings

N-SULFENYLATE-N-METHYL-CARBAMIC ACID ESTERS OF 2-OXIMINO-ALKANECARBOXYLIC ACID NITRILES

The present invention relates to and has for its objects the provision of particular new N-sulfenylated-N-methyl-carbamic acid esters of 2-oximino-alkanecarboxylic acid nitriles, which possess insecticidal, acaricidal, fungicidal or bactericidal properties, active compositions in the form of mixtures of such compounds with solid and liquid dispersible carrier vehicles, and methods for producing such compounds and for using such compounds in a new way especially for combating pests, e.g. insects, acarids, fungi and bacteria, with other and further objects becoming apparent from a study of the within specification and accompanying examples.

It has been disclosed in German Offenlegungsschrift DOS 2,016,623 that N-trihalomethyl-sulfenylated N-methylcarbamidoximes, for example 1-methylthio- (Compound A) and 1-ethylthio-acetaldehyde-O-(N-trichloromethylthio-N-methylcarbamoyl)-oxime (Compound B) and 1-methylthio- (Compound C) and 1-ethylthio-acetaldehyde-O-(N-fluorodichloromethylthio-N-methyl-carbamoyl)-oxime (Compound D), display insecticidal, acaricidal and fungicidal properties.

The present invention provides N-sulfenylated-N-methyl-carbamic acid esters of 2-oximino-alkanecarboxylic acid nitriles of the formula

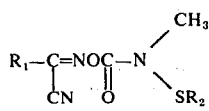

in which
R₁ is alkyl, cycloalkyl, or alkyl-substituted cycloalkyl, and
R₂ is a C₁₋₈ aliphatic radical substituted by halogen; aryl; aryl substituted by halogen, methyl, trifluoromethyl or nitro; or the radical of the formula

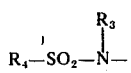

wherein
R₃ is alkyl, and
R₄ is alkyl, haloalkyl, aryl, or aryl substituted by halogen, methyl or nitro.

Preferably, R₁ is alkyl of one to six carbon atoms, cyclohexyl or cycloheptyl optionally substituted by alkyl of one to four carbon atoms such as methyl, and R₂ is chlorine-and/or fluorine-substituted methyl, phenyl, methyl, chlorine-and/or trifluoromethyl-substituted phenyl, or the radical of the formula

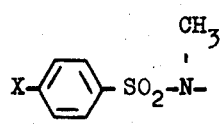

in which
X is chlorine or methyl.

It is distinctly surprising that the compounds according to the invention display a greater insecticidal and acaricidal action than the previously known N-trihalomethylsulfenylated N-methyl-carbamidoximes. In addition to their insecticidal and acaricidal action, the compounds according to the invention are also fungicidally active. The compounds according to the invention thus represent an enrichment of the art.

The invention also provides a process for the production of a N-sulfenylated N-methylcarbamidoxime of the formula (I) in which a N-sulfenylated N-methylcarbamic acid fluoride of the general formula

in which
R₂ has the abovementioned meaning
is reacted with a 2-oximinonitrile of the general formula

in which
R₁ has the abovementioned meaning
in the form of a salt or in the presence of an acid-binding agent, and in the presence of a diluent.

The course of the reaction can be represented by the following equation when using N-(fluorodichloromethylthio)-N-methylcarbamic acid fluoride and 2-oximino-3,3-dimethyl-butyronitrile as starting compounds:

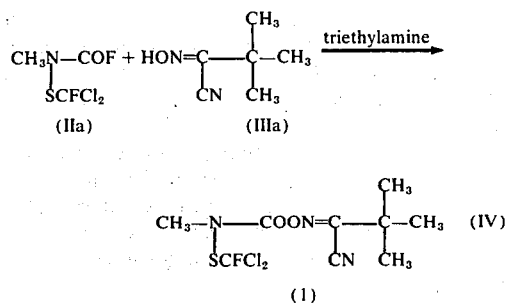

The formula (II) provides a general definition of the N-sulfenylated N-methylcarbamic acid fluorides used as starting products. Some of these compounds are described in German Auslegeschrift DAS 1,297,095, and some may be prepared according to processes described in application Ser. No. 408,253, filed Oct. 19, 1973, now pending, the disclosure of which is incorporated herein by reference. Thus, carbamic acid fluorides, for example N-methyl-(p-toluenesulfonic acid methylamide-N'-sulfenyl)-carbamic acid fluoride, may be obtained by reacting the sodium salt of the corresponding arylsulfonic acid methylamides with disulfur dichloride. The disulfide thus obtained is then split by means of chlorine to give the sulfenic acid chloride and the latter is reacted with N-methyl-carbamic acid fluoride. This method of synthesis is illustrated by the following formula scheme:

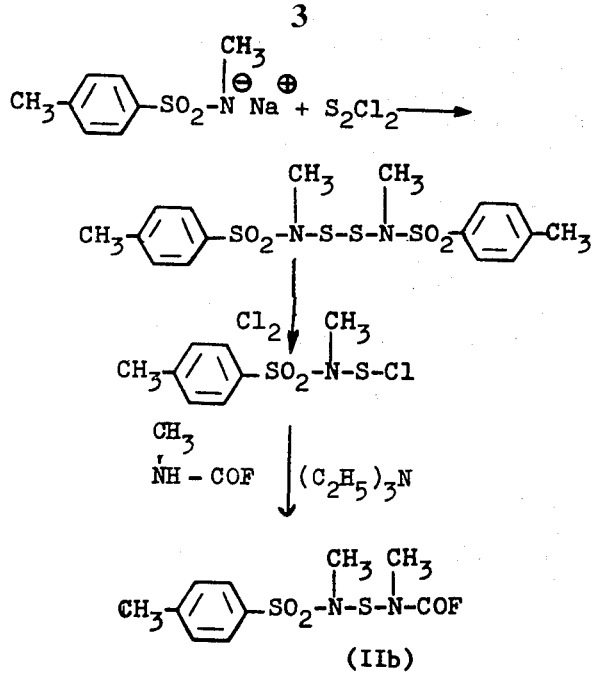

The 2-oximinonitriles required for the reaction, defined by formula (III), are known compounds and are obtained by oxidation of 2-hydroxylaminonitriles as shown in Journal of Organic Chemistry 25, 1471 (1960). They can also be obtained by a process which has not been published, by reacting 2-iminonitriles with salts of hydroxylamine.

The following 2-oximinonitriles are preferred: 2-oximino-propionitrile, -butyronitrile, -valeronitrile, -3,3-dimethylvaleronitrile and -3,3-dimethylbutyronitrile, and 2-oximino-3-methylhexahydrobenzonitrile.

All inert organic solvents can be used as diluents. These include ethers, such as diethyl ether, tetrahydrofuran and dioxane, hydrocarbons, such as benzene, and chlorinated hydrocarbons, such as chloroform and chlorobenzene.

To bind the hydrogen fluoride produced in the reaction, a tertiary base, such as triethylamine, or inorganic bases, such as alkali metal hydroxides or carbonates, are added to the reaction mixture. Alternatively, it is possible to react salts of the oximes in water, especially alkali metal salts.

The reaction temperatures can be varied within a wide range and are in general about 0° to 100°C, preferably 20°–40°C.

In general, equimolar quantities may be used when carrying out the process. In many cases it has proved advantageous to employ the oxime component in a slight excess, e.g. up to about 20 per cent by weight.

The reaction mixture is worked up in the usual manner.

The compounds according to the invention are either obtained in the form of oils of yellow color or are colorless crystalline substances.

The new compounds display excellent insecticidal, acaricidal, fungicidal and bactericidal properties. They are therefore particularly suitable for combating sucking and biting insects, diptera, mites and plant-pathogenic fungi. For this reason they are employed in plant protection and against hygiene pests and pests of stored products. They can also be used as seed dressings.

To the sucking insects there belong, in the main, aphids (Aphidae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly and moth caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*).

Also to be classed with the biting insects are beetles (Coleoptera), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acari) there are classed, in particular, the spider mites (Tetranychidae) such as the two-spotted spider mite (*Tetranychus urticae*) and the European red mite (*Paratetranychus pilosus* = *Panonychus ulmi*), gall mites, for example the blackcurrent gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against hygiene pests and pests of stored products, particularly flies and mosquitoes, the novel products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl celulose, etc.

Such active compounds may be employed alone or in the form of mixtures with one another and/or with such solid and/or liquid dispersible carrier vehicles and/or with other known compatible active agents, especially plant protection agents, such as other insecticides, acaricides, fungicides and bactericides, or rodenticides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e., mist form, for example by airplane crop spraying techniques. Only up to at most about a few liters/hectare are needed, and often amounts only up to about 15 to 1,000 gg/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, acarids, fungi and bacteria, and more particularly methods of combating at least one of insects, acarids and fungi, which comprises applying to at least one of correspondingly (a) such insects, (b) such acarids, (c) such fungi, (d) such bacteria, and (e) the corresponding habitat thereof, i.e., the locus to be protected, a correspondingly combative or toxic amount, i.e., an insecticidally, acaricidally, fungicidally or bactericidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1
Drosophila test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 ml of the preparation of the active compound was applied with a pipette to a filter paper disc of 7 cm diameter. The wet disc was placed in glass vessel containing 50 vinegar flies (*Drosophila melanogaster*) and covered with a glass plate.

After the specified periods of time, the destruction was determined as a percentage: 100% means that all of the flies were killed; 0% means that none of the flies were killed.

The active compounds, their concentrations, the evaluation times and the degree of destruction can be seen from the following table:

Table 1

(insects which damage plants)

Drosophila Test

| Active compounds | Active compound concentration in % | Degree of destruction in % after 1 day |
|---|---|---|
| $CH_3-S-C=NO-CO-N-CH_3$ <br> $\quad\quad\ CH_3 \quad\quad\quad SCCl_3$ <br> (known) (A) | 0.1 | 0 |
| $C_4H_9-S-C=NO-CO-N-CH_3$ <br> $\quad\quad\ CH_3 \quad\quad\quad SCFCl_2$ <br> (known) (E) | 0.1 <br> 0.01 | 90 <br> 0 |
| $(CH_3)_3C-C=NO-CO-N-CH_3$ <br> $\quad\quad\ CN \quad\quad\quad S-CCl_3$ <br> (2) | 0.1 <br> 0.01 | 100 <br> 100 |
| $(CH_3)_3C-C=NO-CO-N-CH_3$ <br> $\quad\quad\ CN \quad\quad\quad SCFCl_2$ <br> (1) | 0.1 <br> 0.01 <br> 0.001 <br> 0.0001 | 100 <br> 100 <br> 100 <br> 100 |
| $\quad\quad\ CH_3$ <br> $C_2H_5-C-C=NO-CO-N-CH_3$ <br> $\quad\quad\ CN \quad\quad\quad SCCl_3$ <br> $\quad\quad\ CH_3 \quad (6)$ | 0.1 <br> 0.01 | 100 <br> 100 |
| $\quad\quad\ CH_3$ <br> $C_2H_5-C-C=NO-CO-N-CH_3$ <br> $\quad\quad\ CH_3\ CN \quad (5)\ SCFCl_2$ | 0.1 <br> 0.01 <br> 0.001 | 100 <br> 100 <br> 100 |
| $C_3H_7-C=NO-CO-N-CH_3$ <br> $\quad\quad\ CN \quad (4)\ SCFCl_2$ | 0.1 <br> 0.01 <br> 0.001 <br> 0.0001 | 100 <br> 100 <br> 100 <br> 100 |

Table 1 (continued)

(insects which damage plants)

Drosophila Test

| Active compounds | Active compound concentration in % | Degree of destruction in % after 1 day |
| --- | --- | --- |
| i-$C_3H_7$-C(CN)=NO-CO-N(CH$_3$)-SCFCl$_2$ (3) | 0.1<br>0.01<br>0.001<br>0.0001 | 100<br>100<br>100<br>100 |
| (CH$_3$)$_2$CH-C(CN)=NO-CO-N(CH$_3$)-S-C$_6$H$_5$ (13) | 0.1<br>0.01<br>0.001 | 100<br>100<br>99 |
| (CH$_3$)$_2$CH-C(CN)=NO-CO-N(CH$_3$)-S-C$_6$H$_4$-CH$_3$ (16) | 0.1<br>0.01 | 100<br>100 |
| $C_3H_7$-C(CN)=NO-CO-N(CH$_3$)-S-C$_6$H$_5$ (14) | 0.1<br>0.01 | 100<br>100 |
| t-$C_4H_9$-C(CN)=NO-CO-N(CH$_3$)-S-C$_6$H$_5$ (10) | 0.1<br>0.01 | 100<br>100 |

EXAMPLE 2

Plutella test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the capterpillars were killed.

The active compounds, the concentrations of the active compounds, the evaluation times and the results can be seen from the following Table:

Table 2

(insects which damage plants)

Plutella Test

| Active compounds | Active compound concentration in % | Degree of destruction in % after 3 days |
| --- | --- | --- |
| $C_4H_9$-S-C(CH$_3$)=NO-CO-N(CH$_3$)-SCFCl$_2$ (E) (known) | 0.1<br>0.01 | 100<br>0 |

Table 2 (continued)

(insects which damage plants)

Plutella Test

| Active compounds | Active compound concentration in % | Degree of destruction in % after 3 days |
| --- | --- | --- |
| $(CH_3)_3C-C(CN)=NO-CO-N(CH_3)(S-CCl_3)$ (2) | 0.1<br>0.01<br>0.001 | 100<br>100<br>100 |
| $(CH_3)_3C-C(CN)=NO-CO-N(CH_3)(SCFCl_2)$ (1) | 0.1<br>0.01<br>0.001 | 100<br>100<br>100 |
| $C_2H_5-C(CH_3)_2-C(CN)=NO-CO-N(CH_3)(S-CCl_3)$ (6) | 0.1<br>0.01<br>0.001 | 100<br>100<br>80 |
| $C_2H_5-C(CH_3)_2-C(CN)=NO-CO-N(CH_3)(SCFCl_2)$ (5) | 0.1<br>0.01<br>0.001 | 100<br>100<br>80 |
| $i-C_3H_7-C(CN)=NO-CO-N(CH_3)(SCFCl_2)$ (3) | 0.1<br>0.01 | 100<br>100 |
| $(CH_3)_2CH-C(CN)=NO-CO-N(CH_3)(S-C_6H_5)$ (13) | 0.1<br>0.01 | 100<br>100 |
| $(CH_3)_2CH-C(CN)=NO-CO-N(CH_3)(S-C_6H_4-CH_3)$ (16) | 0.1<br>0.01 | 100<br>100 |
| $t-C_4H_9-C(CN)=NO-CO-N(CH_3)(S-C_6H_5)$ (10) | 0.1<br>0.01<br>0.001 | 100<br>100<br>100 |
| $t-C_4H_9-C(CN)=NO-CO-N(CH_3)(S-C_6H_4-CF_3)$ (9) | 0.1<br>0.01<br>0.001 | 100<br>100<br>80 |
| $t-C_4H_9-C(CN)=NO-CO-N(CH_3)(S-C_6H_4-Cl)$ (11) | 0.1<br>0.01<br>0.001 | 100<br>100<br>100 |

Table 2 (continued)

(insects which damage plants)

Plutella Test

| Active compounds | Active compound concentration in % | Degree of destruction in % after 3 days |
|---|---|---|
| 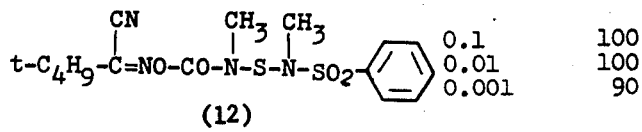 (12) | 0.1<br>0.01<br>0.001 | 100<br>100<br>90 |
| 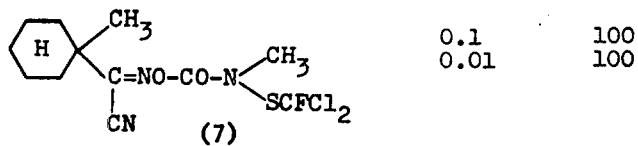 (7) | 0.1<br>0.01 | 100<br>100 |

EXAMPLE 3

Rhopalosiphum test (systemic action)

Solvent: 3 parts by weight of dimethylformamide
Emulsifier: 1 part by weight of alkylaryl polyglycol ether To produce a suitable preparation of active compound 1 part by weight of the active compound was mixed with the stated amount of solvent containing the stated amount of emulsifier and the concentrate was diluted with water to the desired concentration.

Oat plants (*Avena sativa*) which had been strongly infested with the bird cherry aphid (*Rhopalosiphum padi*) were watered with the preparation of the active compound so that the preparation penetrated into the soil without wetting the leaves of the oat plants. The active compound was taken up by the oat plants from the soil and thus reached the infested leaves.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following Table:

Table 3

(insects which damage plants)

Rhopalosiphum test (systemic action)

| Active compounds | Active compound concentration in % | Degree of destruction in % after 4 days |
|---|---|---|
| <br>(known) (B) | 0.1<br>0.01 | 100<br>0 |
| <br>(known) (D) | 0.1<br>0.01 | 100<br>0 |
| <br>(known) (E) | 0.1 | 0 |

Table 3 (continued)

(insects which damage plants)

Rhopalosiphum test (systemic action)

| Active compounds | Active compound concentration in % | Degree of destruction in % after 4 days |
|---|---|---|
| $(CH_3)_3C-C(CN)=NO-CO-N(CH_3)-SCCl_3$ (2) | 0.1<br>0.01 | 100<br>100 |
| $(CH_3)_3C-C(CN)=NO-CO-N(CH_3)-SCFCl_2$ (1) | 0.1<br>0.01 | 100<br>100 |
| $C_2H_5-C(CH_3)(CH_3)-C(CN)=NO-CO-N(CH_3)-SCFCl_2$ (5) | 0.1<br>0.01 | 100<br>100 |
| $t-C_4H_9-C(CN)=NO-CO-N(CH_3)-S-C_6H_5$ (10) | 0.1<br>0.01<br>0.001 | 100<br>100<br>98 |
| $t-C_4H_9-C(CN)=NO-CO-N(CH_3)-S-C_6H_4-Cl$ (11) | 0.1<br>0.01 | 100<br>100 |
| $t-C_4H_9-C(CN)=NO-CO-N(CH_3)-S-C_6H_4-CF_3$ (9) | 0.1<br>0.01 | 100<br>100 |

EXAMPLE 4

Tetranychus test (resistant)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the effectiveness of the preparation of active compound was determined by counting the dead mites. The degree of destruction thus obtained is expressed as a percentage: 100% means that all the spider mites were killed whereas 0% means that none of the spider mites were killed.

The active compounds, the concentrations of the active compounds, the valuation times and the results can be seen from the following Table:

Table 4

(mites which damage plants)

Tetranychus Test (resistant)

| Active compounds | Active compound concentration in % | Degree of destruction in % after 2 days |
|---|---|---|
| $CH_3-C(SC_2H_5)=NO-CO-N(CH_3)-SCCl_3$ (known) (B) | 0.1<br>0.01 | 90<br>0 |

Table 4 (continued)

(mites which damage plants)

Tetranychus Test (resistant)

| Active compounds | Active compound concentration in % | Degree of destruction in % after 2 days |
| --- | --- | --- |
| $(CH_3)_3C-C(CN)=NO-CO-N(CH_3)-SCCl_3$ (2) | 0.1<br>0.01 | 100<br>99 |
| $t-C_4H_9-C(CN)=NO-CO-N(CH_3)-S-C_6H_4-Cl$ (11) | 0.1<br>0.01<br>0.001 | 100<br>100<br>40 |
| $t-C_4H_9-C(CN)=NO-CO-N(CH_3)-S-C_6H_4-CF_3$ (9) | 0.1<br>0.01 | 100<br>100 |
| $t-C_4H_9-C(CN)=NO-CO-N(CH_3)-S-N(CH_3)-SO_2-C_6H_5$ (12) | 0.1<br>0.01 | 100<br>95 |

EXAMPLE 5

LT$_{100}$ test for Diptera

Test insects: *Musca domestica* and *Aedes aegypti*
Solvent: Acetone 2 parts by weight of active compound were dissolved in 1000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound used. About 25 test insects were then placed in the Petri dish and it was covered with a glass lid.

The condition of the test insects was continuously observed. The time which was necessary for a 100% knock down effect was determined.

The test insects, the active compounds, the concentrations of the active compounds and the periods of time at which there was a 100% knock down effect can be seen from the following Table:

Table 5

LT$_{100}$ Test for Diptera

| | Active compounds | Test insects | Active compound concentration of the solution in % | LT$_{100}$ |
| --- | --- | --- | --- | --- |
| Known: | $(CH_3)(C_2H_5S)C=N-O-C(O)-N(CH_3)(SCFCl_2)$ (D) | Musca domestica<br>Aedes aegypti | 0.2<br>0.2 | 8 hrs. = 0<br>3 hrs. = 0 |
| | $(CH_3)(CH_3S)C=N-O-C(O)-N(CH_3)(SCCl_3)$ (A) | Musca domestica<br><br>Aedes aegypti | 0.2<br>0.02<br>0.2<br>0.02<br>0.002 | 105'<br>6 hrs.<br>60'<br>60'<br>3 hrs. = 0 |

Table 5 (continued)

$LT_{100}$ Test for Diptera

| Active compounds | Test insects | Active compound concentration of the solution in % | $LT_{100}$ |
|---|---|---|---|

According to the invention:

| | | | |
|---|---|---|---|
| (CH$_3$)$_3$C-C(CN)=N-O-C(O)-N(CH$_3$)(SCFCl$_2$)  (1) | Musca domestica<br>Aedes aegypti | 0.002<br>0.00002 | 60'<br>120' |
| (CH$_3$)$_3$C-C(CN)=N-O-C(O)-N(CH$_3$)(SCCl$_3$)  (2) | Musca domestica<br>Aedes aegypti | 0.002<br>0.0002 | 50'<br>60' |
| i-C$_3$H$_7$-C(CN)=N-O-C(O)-N(CH$_3$)(SCFCl$_2$)  (3) | Musca domestica<br>Aedes aegypti | 0.002<br>0.002 | 60'<br>60' |
| C$_2$H$_5$-C(CH$_3$)$_2$-C(CN)=N-O-C(O)-N(CH$_3$)(SCFCl$_2$)  (5) | Musca domestica<br>Aedes aegypti | 0.02<br>0.002 | 75'<br>120' |
| C$_4$H$_9$-t-C(CN)=N-O-C(O)-N(CH$_3$)(S-C$_6$H$_5$)  (10) | Musca domestica<br>Aedes aegypti | 0.02<br>0.0002 | 80'<br>3 hrs. |
| C$_4$H$_9$-t-C(CN)=N-O-C(O)-N(CH$_3$)(S-C$_6$H$_4$-Cl)  (11) | Musca domestica<br>Aedes aegypti | 0.02<br>0.0002 | 145'<br>3 hrs. |
| C$_4$H$_9$-t-C(CN)=N-O-C(O)-N(CH$_3$)(S-C$_6$H$_4$-CF$_3$)  (9) | Musca domestica<br>Aedes aegypti | 0.02<br>0.0002 | 90'<br>3 hrs. |
| (CH$_3$)$_2$CH-C(CN)=N-O-C(O)-N(CH$_3$)(S-C$_6$H$_5$)  (13) | Musca domestica<br>Aedes aegypti | 0.002<br>0.0002 | 3 hrs.<br>120' |
| C$_3$H$_7$-C(CN)=N-O-C(O)-N(CH$_3$)(S-C$_6$H$_5$)  (14) | Musca domestica<br>Aedes aegypti | 0.02<br>0.002 | 3 hrs.<br>120' |
| (CH$_3$)$_2$CH-C(CN)=N-O-C(O)-N(CH$_3$)(S-C$_6$H$_4$-Cl)  (15) | Musca domestica<br>Aedes aegypti | 0.02<br>0.002 | 60'<br>120' |
| C$_2$H$_5$-C(CH$_3$)$_2$-C(CN)=N-O-C(O)-N(CH$_3$)(SCCl$_3$)  (6) | Musca domestica<br>Aedes aegypti | 0.02<br>0.002 | 65'<br>60' |

EXAMPLE 6

Mycelium growth test

Nutrient medium used:
 20 parts by weight of agar-agar
 200 parts by weight of potato decoction
 5 parts by weight of malt
 15 parts by weight of dextrose
 5 parts by weight of peptone
 2 parts by weight of $Na_2HPO_4$
 0.3 part by weight of $Ca(NO_3)_2$
Proportion of solvent to nutrient medium:
 2 parts by weight of solvent mixture
 100 parts by weight of agar nutrient medium
Composition of solvent mixture
 0.19 part by weight of DMF or acetone
 0.01 part by weight of emulsifier Emulvin W
 <u>1.80 parts by weight of water</u>
 2 parts by weight of solvent mixture The amount of active compound required for the desired concentration of active compound in the nutrient medium was mixed with the stated amount of solvent. The concentrate was thoroughly mixed, in the stated proportion, with the liquid nutrient medium (which had been cooled to 42°C) and was then poured into Petri dishes of 9 cm diameter. Control dishes to which the preparation had not been added were also set up.

When the nutrient medium had cooled and solidified, the dishes were inoculated with the species of fungi stated in Table 6 and incubated at about 21°C.

Evaluation was carried out after 4–10 days, dependent upon the speed of growth of the fungi. When evaluation was carried out the radial growth of the mycelium on the treated nutrient media was compared with the growth on the control nutrient media. In the evaluation of the fungus growth, the following characteristic values are used:

```
          1 no fungus growth
    up to 3 very strong inhibition of growth
    up to 5 medium inhibition of growth
    up to 7 slight inhibition of growth
          9 growth equal to that of untreated control
```

The active compounds, their concentrations and the results obtained can be seen from the following Table:

Table 6

Mycelium growth test
(Active compound concentration 10 ppm)

Fungi and one bacterium

| Active compounds | Piricularia oryzae | Phialophora cinerescens | Pellicularia sasakii | Mycosphaerella musicola | Verticillium alboatrum | Fusarium dianthi | Cochliobolus miyabeanus | Colletotrichum coffeanum | Xanthomonas oryzae |
|---|---|---|---|---|---|---|---|---|---|
| $CH_3-C=NOCONCH_3$ <br> $\quad\;\; \mid \qquad\qquad \mid$ <br> $\quad SC_2H_5 \;\; SCCl_3$ <br> (known) (B) | 9 | 9 | 9 | – | 9 | 9 | 9 | 9 | 9 |
| $CH_3-N-COON=C-SCH_3$ <br> $\quad\;\; \mid \qquad\qquad\;\; \mid$ <br> $\quad SCCl_3 \quad\;\; CH_3$ <br> (known) (A) | 9 | 9 | 9 | 9 | 9 | 9 | 9 | 9 | 9 |
| $(CH_3)_3C-C=NO-CO-N-CH_3$ <br> $\qquad\quad \mid \qquad\qquad\;\; \mid$ <br> $\qquad\quad CN \quad\;\; SCFCl_2$ (1) | 1 | 1 | 1 | 1 | 1 | – | 1 | 1 | 1 |
| $i\text{-}C_3H_7-C=NO-CO-N\!\!<\!\!^{CH_3}_{S\text{-}CFCl_2}$ <br> $\qquad\quad\;\; \mid$ <br> $\qquad\quad\;\; CN$ (3) | 1 | 1 | 1 | 1 | 1 | – | 1 | 1 | 1 |
| $\quad\;\; CH_3$ <br> $\quad\;\;\mid$ <br> $C_2H_5-C\!-\!-\!-\!C=NO-CO-N\!\!<\!\!^{CH_3}_{SCFCl_2}$ <br> $\quad\;\;\mid \qquad \mid$ <br> $\quad\;\; CH_3 \;\; CN$ (5) | 1 | 1 | 1 | 1 | 1 | – | 1 | 1 | 1 |
| $C_3H_7-C=NO-CO-N\!\!<\!\!^{CH_3}_{SCFCl_2}$ <br> $\qquad\;\; \mid$ <br> $\qquad\;\; CN$ (4) | 1 | 1 | 1 | 1 | 1 | – | 1 | 1 | 1 |
| $\langle H \rangle\!\!<\!\!^{CH_3}_{C=NO-CO-N<^{CH_3}_{SCFCl_2}}$ <br> $\qquad\;\; \mid$ <br> $\qquad\;\; CN$ (7) | 1 | 2 | 1 | 1 | 3 | – | 1 | 1 | – |

EXAMPLE 7

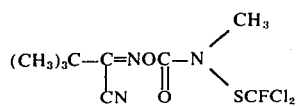 (1)

11.4 g (0.1 mole) of 2-oximino-3,3-dimethylbutyronitrile and 21 g (0.1 mole) of N-(fluorodichloromethylmercapto)-methylcarbamic acid fluoride were dissolved in 100 ml of dioxane and 11 g of triethylamine were added dropwise at room temperature. In the course thereof, the temperature rose to about 40°C. After completion of the reaction, water was added in the cold and the oil which thereupon separated out was taken up in ether. After drying, the ether solution was concentrated. The residue which crystallized slowly was recrystallized from aqueous methanol. Yield 22 g. Melting point 40° – 41°C.

The following compounds were obtained analogously

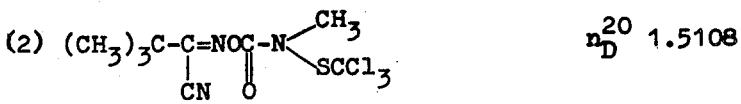 $n_D^{20}$ 1.5108

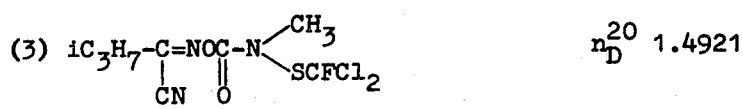 $n_D^{20}$ 1.4921

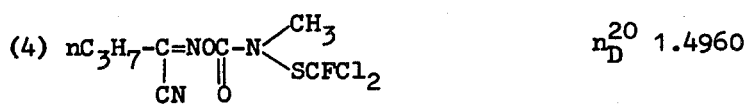 $n_D^{20}$ 1.4960

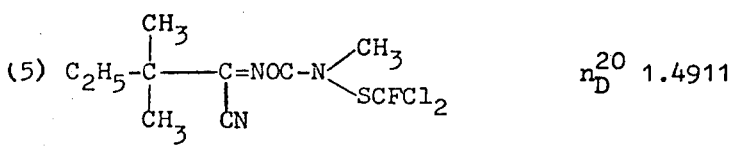 $n_D^{20}$ 1.4911

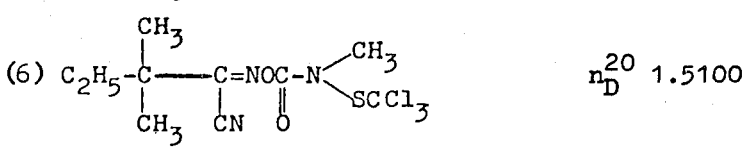 $n_D^{20}$ 1.5100

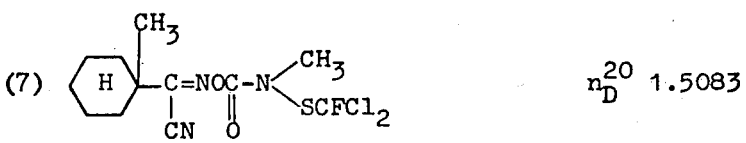 $n_D^{20}$ 1.5083

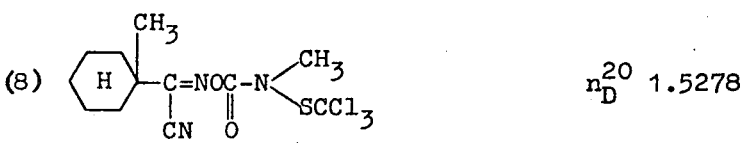 $n_D^{20}$ 1.5278

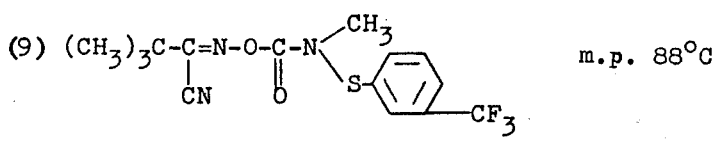 m.p. 88°C

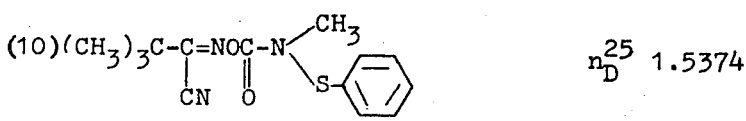 $n_D^{25}$ 1.5374

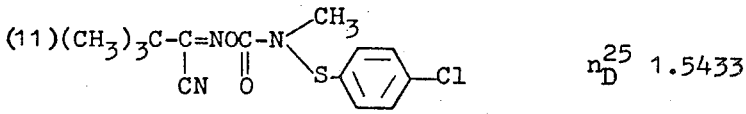 $n_D^{25}$ 1.5433

(12) 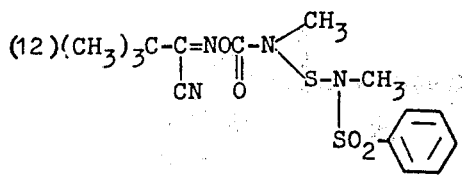　　m.p. 76°C

(13) 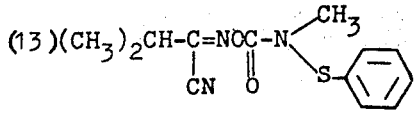　　$n_D^{25}$ 1.5443

(14) 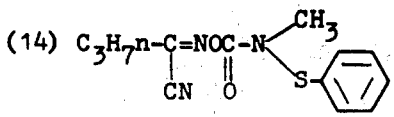　　$n_D^{25}$ 1.5478

(15) 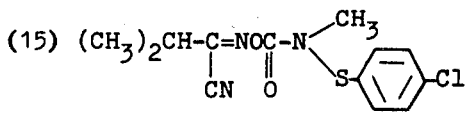　　$n_D^{25}$ 1.5603

(16) 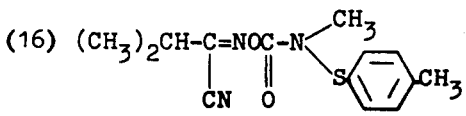　　$n_D^{25}$ 1.5432

Other compounds which may be similarly prepared include the:
  N-(2-nitrophenylmercapto)-N-methyl-carbamic acid ester of 2-oximino-propionitrile,
  N-(N'-isopropyl-N'-t-butyl-sulfonamidomercapto)-N-methyl-carbamic acid ester of 2-oximino-octanoic acid nitrile,
  N-(N'-ethyl-N'-2-bromoethylsulfonamidomercapto)-N-methyl-carbamic acid ester of 2-cycloheptyl-2-oximinoacetonitrile,
and the like.

It will be appreciated that the instant specification and examples are set forth by way of illustration and not limitation, and that various modifications and changes may be made without departing from the spirit and scope of the present invention.

What is claimed is:
1. An N-sulfenylated-N-methylcarbamic acid ester of a 2-oximino-alkanecarboxylic acid nitrile of the formula

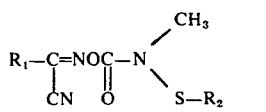　　(1)

in which
  R$_1$ is alkyl of one to six carbon atoms, or cyclohexyl or cycloheptyl optionally substituted by alkyl of one to four carbon atoms, and
  R$_2$ is methyl substituted by at least one of fluoro of chloro, phenyl, methylphenyl, fluorophenyl, trifluoromethylphenyl, or the radical of the formula

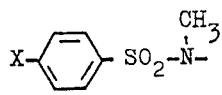

in which
  X is chlorine or methyl.

2. A compound according to claim 1 in which R$_1$ is alkyl of one to six carbon atoms, or cyclohexyl or cycloheptyl optionally substituted by alkyl of one to four carbon atoms, and R$_2$ is chloromethyl, fluoromethyl, phenyl, methylphenyl, fluorophenyl, trifluoromethylphenyl, or the radical of the formula

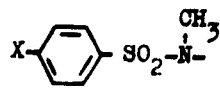

in which
  X is chlorine or methyl.

3. The compound according to claim 1 wherein such compound is N-(fluorodichloro-methylmercapto)-N-methyl-carbamic acid ester of 2-oximino-3-methyl-butyronitrile of the formula

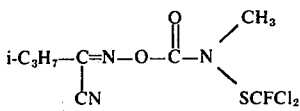

4. The compound according to claim 1 wherein such compound is N-(3-trifluoromethylphenylmercapto)-N-methyl-carbamic acid ester of 2-oximino-3,3-dimethyl-butyronitrile of the formula

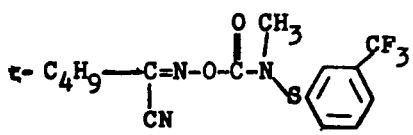

5. The compound according to claim 1 wherein such compound is N-(4-chlorophenylmercapto)-N-methyl-carbamic acid ester of 2-oximino-3,3-di-methyl-butyronitrile of the formula

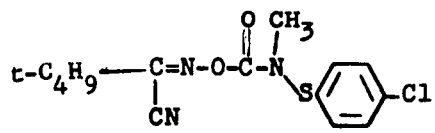

6. The compound according to claim 1 wherein such compound is N-phenylmercapto-N-methyl-carbamic acid ester of 2-oximino-valeronitrile of the formula

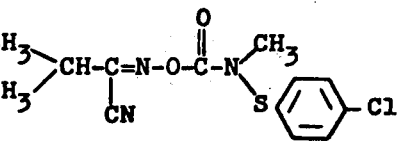

7. The compound according to claim 1 wherein such compound is N-(4-chlorophenylmercapto)-N-methyl-carbamic acid ester of 3-methyl-butyronitrile of the formula

* * * * *